United States Patent
Narita et al.

(10) Patent No.: US 10,350,236 B2
(45) Date of Patent: Jul. 16, 2019

(54) CHONDROITIN SULFATE DERIVATIVE AND AGENT FOR TREATING BLADDER DISEASES

(71) Applicant: Seikagaku Corporation, Tokyo (JP)

(72) Inventors: Muneto Narita, Tokyo (JP); Takahiro Hatanaka, Tokyo (JP); Yuko Yoshida, Tokyo (JP)

(73) Assignee: Seikagaku Corporation, Tokyo (JP)

( * ) Notice: Subject to any disclaimer, the term of this patent is extended or adjusted under 35 U.S.C. 154(b) by 77 days.

(21) Appl. No.: 15/542,226

(22) PCT Filed: Jan. 8, 2016

(86) PCT No.: PCT/JP2016/050526
§ 371 (c)(1),
(2) Date: Jul. 7, 2017

(87) PCT Pub. No.: WO2016/111356
PCT Pub. Date: Jul. 14, 2016

(65) Prior Publication Data
US 2017/0354675 A1 Dec. 14, 2017

(30) Foreign Application Priority Data
Jan. 9, 2015 (JP) ................................ 2015-003572

(51) Int. Cl.
*A61K 47/54* (2017.01)
*A61K 31/573* (2006.01)
*A61K 31/737* (2006.01)

(52) U.S. Cl.
CPC .......... *A61K 31/737* (2013.01); *A61K 31/573* (2013.01); *A61K 47/542* (2017.08)

(58) Field of Classification Search
None
See application file for complete search history.

(56) References Cited

U.S. PATENT DOCUMENTS

| | | |
|---|---|---|
| 6,083,933 A | 7/2000 | Hahn |
| 2016/0151506 A1 | 6/2016 | Miyamoto et al. |
| 2016/0158369 A1 | 6/2016 | Sato et al. |

FOREIGN PATENT DOCUMENTS

| | | |
|---|---|---|
| WO | 2015/005458 A1 | 1/2015 |
| WO | 2015/005459 A1 | 1/2015 |

OTHER PUBLICATIONS

Xin et al., "The Use of Amino Acid Linkers in the Conjugation of Paclitaxel with Hyaluronic Acid as Drug Delivery System: Synthesis, Self-Assembled Property, Drug Release, and In Vitro Efficiency" Pharmaceutical Research vol. 27 No. 2 pp. 380-389 (Year: 2010).*
H. Onishi et al. "Conjugate between Chondroitin Sulfate and Prednisolone with a Glycine Linker: Preparation and in Vitro Conversion Analysis", Chemical and Pharmaceutical Bulletin, Jan. 1, 2013, vol. 61, No. 9, pp. 902-912 (11 pages).
I. Offiah et al. "Interstitial cystitis/bladder pain syndrome: diagnosis and management", International Urogynecology Journal, Feb. 22, 2013, vol. 24, No. 8, pp. 1243-1256 (14 pages).
Extended European Search Report issued in European Application No. 16735095.8, dated Jun. 11, 2018 (8 pages).
Onishi, Hiraku, et al., "In vivo evaluation of chondroitin sulfate-glycyl-prednisolone for anti-arthritic effectiveness and pharmacokinetic characteristics"; International Journal of Pharmaceutics; vol. 456, (2013); pp. 113-120.
Guidelines for the Diagnosis and Examination of Interstitial Cystitis; Society of Interstitial Cystitis of Japan, Guideline Preparation Committee, ed., (Jan. 10, 2007), with a partial English translation (17 pages).
"Diagnosis and Treatment of Interstitial Cystitis/Bladder Pain Syndrome"; American Urological Association (AUA) Guideline; Sep. 2014 (45 pages).
Department of Drug Delivery Research, Hoshi University, Section P24-12 of the APSTJ (Academy of Pharmaceutical Science and Technology, Japan) journal; p. 207, with a partial English translation (8 pages).
International Search Report issued in PCT/JP2016/050526 dated Mar. 15, 2016 (2 pages).
Written Opinion of the International Searching Authority issued in PCT/JP2016/050526 dated Mar. 15, 2016 (4 pages).
Onishi, H. et al.; "Chondroitin Sulfate-Glycyl-Prednisolone Conjugate as Arthritis Targeting System: Localization and Drug Release in Inflammatory Joints"; Biological & Pharmaceutical Bulletin, vol. 37, No. 10, 2014, pp. 1641-1649 (9 pages).
Yu, C. et al.; "Redox-responsive shell-sheddable micelles self-assembled from amphiphilic chondroitin sulfate-cholesterol conjugates for triggrered intracellular drug release"; Chemical Engineering Journal, 228, 2013, pp. 290-299 (10 pages).

* cited by examiner

*Primary Examiner* — Eric Olson
(74) *Attorney, Agent, or Firm* — Osha Liang LLP (57) ABSTRACT

Provided is a compound in which a group derived from chondroitin sulfate and a group derived from a steroid are covalently bonded together via a spacer represented by general formula (I). In the formula, m represents an integer of 0 or 1. Here, if m=0, $R^1$ represents a group selected from the group consisting of electron-donating groups and steric hindrance groups. If m=1, $R^1$ represents a group selected from the group consisting of a hydrogen atom, electron-donating groups and steric hindrance groups.

$$-HN-(CH_2)_m-CHR^1-CO- \quad (I)$$

8 Claims, 2 Drawing Sheets

CHONDROITIN SULFATE DERIVATIVE AND AGENT FOR TREATING BLADDER DISEASES

TECHNICAL FIELD

The present invention relates to a chondroitin sulfate derivative and an agent for treating bladder diseases that contains the chondroitin sulfate derivative.

BACKGROUND ART

Bladder diseases such as interstitial cystitis (IC) are intractable diseases presenting with symptoms such as chronic micturition and urinary urgency. However, since the cause of interstitial cystitis has yet to be determined, the treatment thereof is dependent upon symptomatic or empirical methods, and a definitive treatment has yet to be established despite various attempts.

In relation thereto, chondroitin sulfate (see, for example, U.S. Pat. No. 6,083,933 or International Journal of Pharmaceutics (Ohnishi, et al., Vol. 456, pp. 113-120, 2013)) and steroids (see, for example, Guidelines for the Diagnosis and Examination of Interstitial Cystitis (Society of Interstitial Cystitis of Japan, Guideline Preparation Committee, ed., Jan. 10, 2007) or American Urological Association (AUA) Guideline, DIAGNOSIS AND TREATMENT OF INTERSTITIAL CYSTITIS/BLADDER PAIN SYNDROME (September 2014)) have been reported to be able to be used as therapeutic agents for the bladder disease of interstitial cystitis. However, although chondroitin sulfate is expected to demonstrate repair effects on the deficient glycosaminoglycan layer, there is little evidence of its efficacy and guidelines recommend that it not be used. In addition, steroids are associated with considerable adverse side effects, there is little evidence for their efficacy, and there is no basis for their recommendation (see, for example, Guidelines for the Diagnosis and Examination of Interstitial Cystitis, Society of Interstitial Cystitis of Japan, Guideline Preparation Committee, ed., (Jan. 10, 2007)).

On the other hand, a compound obtained by bonding a group derived from a type of steroid in the form of prednisolone to a group derived from chondroitin sulfate via a glycine residue (referred to as chondroitin sulfate-glycyl-prednisolone) is known to have antiarthritic activity (see, for example, International Journal of Pharmaceutics (Ohnishi, et al., Vol. 456, pp. 113-120, 2013)).

PRIOR ART LITERATURES

Patent Literature

Patent Literature 1 U.S. Pat. No. 6,083,933

Non Patent Literatures

Non Patent Literature 1 Ohnishi, et al., International Journal of Pharmaceutics, Vol. 456, pp. 113-120, 2013

Non Patent Literature 2 Guidelines for the Diagnosis and Examination of Interstitial Cystitis, Society of Interstitial Cystitis of Japan, Guideline Preparation Committee, ed., (Jan. 10, 2007)

Non Patent Literature 3 American Urological Association (AUA) Guideline, DIAGNOSIS AND TREATMENT OF INTERSTITIAL CYSTITIS/BLADDER PAIN SYNDROME (September 2014)

SUMMARY OF INVENTION

Problems to be Solved by the Invention

However, International Journal of Pharmaceutics (Ohnishi, et al., Vol. 456, pp. 113-120, 2013) does not describe or suggest bladder diseases and also does not disclose or suggest chondroitin sulfate having a specific structure described hereinafter.

An object of the present invention is to provide a chondroitin sulfate derivative capable of reducing the systemic adverse side effects associated with steroids alone and demonstrating greater efficacy than chondroitin sulfate or steroids alone, a pharmaceutical composition containing that compound, and an agent for treating bladder diseases containing that compound.

Means for Solving the Problems

As a result of conducting extensive studies to solve the above-mentioned problems, the inventors of the present invention discovered a compound in which a group derived from chondroitin sulfate (CS) is covalently bonded to a group derived from a steroid via a spacer having a specific structure, and found that this compound demonstrates reduced systemic adverse side effects attributable to steroids and effect of more effectively improving bladder disease than CS or steroids alone by sustaining its pharmaceutical efficacy for a long period of time, thereby leading to completion of the present invention. In addition, the inventors of the present invention also found that the systemic adverse side effects associated with steroids can be reduced by selecting a spacer having specific properties and interposing that spacer between a covalently bonded group derived from CS and group derived from a steroid, thereby also leading to completion of the present invention.

Namely, specific means for solving the above-mentioned problems are as indicated below, and the present invention includes the following aspects.

<1> A compound in which a group derived from CS and a group derived from a steroid are covalently bonded together via a spacer represented by general formula (I):

$$-\text{HN}-(\text{CH}_2)_m-\text{CHR}^1-\text{CO}- \quad (\text{I})$$

(in the formula, m represents an integer of 0 or 1, in the case m=0, $R^1$ represents a group selected from a group consisting of electron-donating groups and steric hindrance groups, and in the case m=1, R' represents a group selected from a group consisting of a hydrogen atom, electron-donating groups and steric hindrance groups).

<2> The compound described in <1>, wherein the electron-donating groups and the steric hindrance groups represented by $R^1$ are groups selected from a group consisting of linear alkyl groups having 1 to 12 carbon atoms, branched alkyl groups having 3 to 12 carbon atoms, cyclic alkyl groups having 3 to 12 carbon atoms, aryl groups having 6 to 10 carbon atoms, alkenyl groups having 2 to 12 carbon atoms, alkynyl groups having 2 to 12 carbon atoms, and aralkyl groups having 7 to 12 carbon atoms.

<3> The compound described in <1> or <2>, wherein, in general formula (I), m=1 and $R^1$ represents a hydrogen atom, or m=0 and $R^1$ represents a methyl group, branched alkyl group having 3 to 4 carbon atoms or benzyl group.

<4> The compound described in any of <1> to <3>, wherein, in general formula (I), m=1 and R' represents a hydrogen atom, or m=0 and $R^1$ represents a sec-butyl group.

<5> A pharmaceutical composition containing the compound described in any of <1> to <4>.

<6> An agent for treating bladder diseases containing the compound described in any of <1> to <4>.

<7> A use of the compound described in any of <1> to <4> in the treatment of bladder diseases.

<8> A method for treating bladder diseases including administration of the agent for treating bladder diseases described in <6> to a subject.

<9> A urinary function ameliorant containing the compound described in any of <1> to <4>.

<10> A use of the compound described in any of <1> to <4> in the improvement of urinary function.

<11> A method for improving urinary function including administration of the urinary function ameliorant described in <9> to a subject.

<12> A compound in which a group derived from CS and a group derived from a steroid are covalently bonded together via a spacer, wherein the spacer exhibits a lower release rate of the steroid from the compound in comparison with the case of using a glycine residue as a spacer in the compound.

<13> The compound described in <12>, wherein the spacer exhibits an equal or lower release rate of the steroid from the compound in comparison with the case of using a β-alanine residue as a spacer in the compound.

<14> A method for producing a compound in which a group derived from CS and a group derived from a steroid are covalently bonded together via a spacer, including at least following steps 1 and 2:

step 1: selecting a spacer with which the release rate of the steroid from the compound is lower in comparison with the case of selecting a glycine residue as a spacer in the compound; and step 2: covalently bonding the group derived from CS and the group derived from the steroid via the spacer selected in step 1.

<15> The method described in <14>, wherein the spacer selected in step 1 exhibits an equal or lower release rate of the steroid from the compound in comparison with the case of selecting a β-alanine residue as a spacer in the compound.

Meanwhile, the above-mentioned aspects <14> and <15> can also be made to be a method for producing a pharmaceutical composition, a method for producing an agent for treating bladder diseases, and a method for producing a urinary function ameliorant, which contain the compound, and the present invention includes such aspects. In this case, a step for incorporating pharmaceutically acceptable components according to the object of production (pharmaceutical composition, agent for treating bladder diseases or urinary function ameliorant) can be further included.

Effects of the Invention

According to the present invention, a chondroitin sulfate derivative capable of reducing systemic adverse side effects associated with steroids alone and demonstrating greater efficacy than CS or steroids alone, a pharmaceutical composition containing that compound, and an agent for treating bladder diseases containing that compound, can be provided.

Modes for Carrying Out the Invention

The term "step" in the present specification not only refers to an independent step, but also includes a step that cannot be clearly distinguished from another step provided the intended objective of that step is achieved. In addition a range of numerical values indicated using "to" indicates a range that includes the values described before and after the "to" as minimum and maximum values thereof, respectively. Moreover, unless specifically indicated otherwise, the content of each component of a composition refers to the total amount of a plurality of those substances present in the composition in the case a plurality of types of the substances are present for each component in the composition.

The following provides a more detailed explanation of the present invention using embodiments thereof.

(1) Chondroitin Sulfate Derivative

The compound according to the present invention in the form of a chondroitin sulfate derivative has a group derived from CS and a group derived from a steroid covalently bonded together via a spacer represented by general formula (I).

$$-\text{HN}-(\text{CH}_2)_m-\text{CHR}^1-\text{CO}- \quad (I)$$

In the formula, m represents an integer of 0 or 1, in the case m=0, R' represents a group selected from a group consisting of electron-donating groups and steric hindrance groups, and in the case m=1, R' represents a group selected from a group consisting of a hydrogen atom, electron-donating groups and steric hindrance groups.

The chondroitin sulfate derivative obtained by covalently bonding a group derived from CS and a group derived from a steroid via a spacer having a specific structure is able to reduce systemic adverse side effects associated with steroids alone and sustain an anti-inflammatory effect or immunosuppressive action over a long period of time. The chondroitin sulfate derivative is able to achieve an especially superior effect as an agent for treating bladder diseases. In the chondroitin sulfate derivative, since the spacer has a specific structure, systemic adverse side effects attributable to steroids alone can be reduced and pharmaceutical efficacy can be sustained locally, thereby enabling the demonstration of superior effects as an agent for treating bladder diseases in particular.

The chondroitin sulfate derivative contains at least one type of group derived from CS. Herein, a group derived from CS refers to a group formed by the removal of a hydroxyl group from the carboxyl group of CS.

There are no particular limitations on the CS that composes the chondroitin sulfate derivative provided it has a structure in which a sulfate group is retained in an oligosaccharide skeleton formed by repeating disaccharides consisting of D-glucuronic acid (or D-iduronic acid) and N-acetyl-D-galactosamine in disaccharide units. In addition, acidic functional groups including the carboxyl group and sulfate group present in CS may be in a free state without forming a salt or may form a pharmaceutically acceptable salt.

Examples of pharmaceutically acceptable salts include salts with alkaline metal ions such as sodium salt or potassium salt, and alkaline earth metal ions such as magnesium salt or calcium salt. CS is preferably in the form of a pharmaceutically acceptable salt with an alkaline metal ion and more preferably in the form of a sodium salt from the viewpoints of applicability and compatibility with the living body.

The CS that composes the chondroitin sulfate derivative can be produced by a known method according to the type thereof. For example, CS can be produced by extraction and purification from an animal-derived raw material, culturing and purification from a chondroitin-producing microorganism and the like, oligosaccharide modification or oligosaccharide synthesis.

There are no particular limitations on the weight average molecular weight of the CS and can be suitably selected according to the objective and the like. The weight average molecular weight is preferably 500 to 120,000, more preferably 2,500 to 60,000 and even more preferably 10,000 to 40,000. Weight average molecular weight of CS can be measured by light scattering.

The chondroitin sulfate derivative contains at least one type of group derived from a steroid. Herein, a group derived from a steroid refers to a group formed by the removal of a hydrogen atom from a hydroxyl group of a steroid molecule. There are no particular limitations on the site from which the hydrogen atom is removed.

There are no particular limitations on the type of steroid that composes the chondroitin sulfate derivative, and can be suitably selected according to the objective and the like. Specific examples of steroids include prednisolone, betamethasone, triamcinolone, triamcinolone acetonide, budesonide and fluticasone, and at least one type selected from this group is used preferably.

One type of steroid may be used alone or two or more types may be used in combination.

The covalent bond between the group derived from a steroid and the spacer is preferably a covalent bond that can be decomposed in the living body and is folioed by a condensation reaction from the viewpoint of controlling the release rate of the steroid from the chondroitin sulfate derivative, and is more preferably an ester bond. The steroid is released as a result of the covalent bond between the group derived from a steroid and the spacer being decomposed (and preferably by solvolysis). The steroid may also be released by decomposing the covalent bond between the group derived from a steroid and the spacer after having decomposed the covalent bond between the group derived from CS and the spacer.

In the chondroitin sulfate derivative, the group derived from CS and the spacer (13 HN—$(CH_2)_m$—$CHR^1$—CO—) are preferably covalently bonded with an amide bond, while the group derived from a steroid and the spacer are preferably covalently bonded with an ester bond. Namely, the compound that forms the spacer (hereinafter, also be referred to as the spacer-forming molecule) is preferably a compound having a structure containing a carboxyl group and an amino group in the molecular structure thereof (such as an amino acid). The chondroitin sulfate derivative formed by amide bonding between a carboxyl group of CS and an amino group of the spacer-forming molecule and by ester bonding between a hydroxyl group of the steroid and a carboxyl group of the spacer-forming molecule is preferable.

The spacer is a divalent linking group represented by general formula (I). In general formula (I), m represents an integer of 0 or 1. Here, in the case m=0, $R^1$ represents an electron-donating group or a steric hindrance group. In the case m=1, $R^1$ represents a hydrogen atom, electron-donating group or steric hindrance group. The value of m and the presence or absence of the electron-donating group or steric hindrance group of $R^1$ has an effect on the decomposition rate of the ester bond between the group derived from a steroid and the spacer. In the case m=0, the ester bond is more susceptible to decomposition than in the case m=1, and the release rate of the steroid from the chondroitin sulfate derivative tends to increase.

The term "steric hindrance group" used in the present specification refers to a bulky group that sterically hinders a chemical reaction such as solvolysis. In general, if $R^1$ of the spacer is substituted with an electron-donating group or steric hindrance group, the covalent bond between the group derived from a steroid and the spacer becomes more difficult to decompose than in the case $R^1$ is a hydrogen atom, thereby resulting in a decrease in the release rate of the steroid. A decrease in release rate can be suitably measured by a method described hereinafter.

There are no particular limitations on the electron-donating group or steric hindrance group provided it can be introduced for $R^1$, and can be suitably selected from commonly used electron-donating groups or steric hindrance groups. Specific examples thereof include linear alkyl groups having 1 to 12 carbon atoms such as a methyl group, ethyl group, propyl group or butyl group; branched alkyl groups having 3 to 12 carbon atoms such as an isopropyl group, isobutyl group, sec-butyl group or tert-butyl group; cyclic alkyl groups having 3 to 6 carbon atoms such as a cyclohexyl group; aryl groups having 6 to 10 carbon atoms such as a phenyl group or tolyl group; alkenyl groups having 2 to 12 carbon atoms such as a vinyl group or allyl group; alkynyl groups having 2 to 12 carbon atoms; and aralkyl groups having 7 to 12 carbon atoms such as a benzyl group. Among these groups, the electron-donating group or steric hindrance group is preferably a group selected from a group consisting of a methyl group, branched alkyl groups having 3 to 4 carbon atoms, a benzyl group and the like. Specific examples of the spacer-forming molecule that can be used include amino acids such as β-alanine, isoleucine, alanine, valine, leucine or phenylalanine, at least one type of amino acid selected from this group is preferable, and at least one type of amino acid selected from a group consisting of β-alanine, isoleucine, valine and leucine is more preferable.

In addition, other amino acids having a substituent other than those listed above can also be used for the above-mentioned spacer-forming molecule. Examples of other amino acids that can be used include arginine, asparagine, serine, aspartic acid, cysteine, glutamine, glutamic acid, proline, tyrosine, tryptophan, lysine, methionine, threonine, histidine and the like.

One type of spacer-forming molecule may be used alone or two or more types may be used in combination.

The spacer represented by general formula (I) is preferably an amino acid residue represented by —HN—$(CH_2)_2$—CO—, —HN—$CH(CH(CH_3)CH_2CH_3)$—CO—, —HN—$CH(CH(CH_3)_2)$—CO— or —HN—$CHCH_2(CH(CH_3)_2)$—CO—, and more preferably —HN—$(CH_2)_2$—CO— or —HN—$CH(CH(CH_3)CH_2CH_3)$—CO—, from the viewpoint of efficacy as an agent for treating bladder diseases and inhibiting adverse side effects. In other words, the spacer-forming molecule is preferably β-alanine, isoleucine, valine or leucine, and more preferably β-alanine or isoleucine.

The chondroitin sulfate derivative can adopt various structures according to, for example, the structure of CS. Specific examples of the structure of the chondroitin sulfate derivative include structures containing at least one type of structural unit represented by chemical formula (II).

In formula (II), although $R^{11}$ respectively and independently represents a hydrogen atom or a sodium salt of a sulfate group, the cation portion of the salt of the sulfate group is not limited to the exemplified sodium. In addition, the number of salts of a sulfate group represented by $R^{11}$ is 0 to 4 and preferably 0 to 3. $R^{13}$ represents a group selected from a group consisting of steric hindrance groups and electron-donating groups, and $R^{14}$ represents a group selected from a group consisting of a hydrogen atom, steric hindrance groups and electron-donating groups.

The chondroitin sulfate derivative may contain only one type of the structural unit represented by the above-mentioned chemical formula, or may contain two or more types in an arbitrary ratio and arbitrary positional relationship. The chondroitin sulfate derivative preferably further contains a structural unit normally contained in CS in addition to the structural unit represented by the above-mentioned chemical formula. Examples of structural units normally contained in CS include structural units in which $R^{12}$ represents ONa or OH in formula (II). However, the cation portion of the salt is not limited to the exemplified sodium.

The content ratio (weight ratio) of the steroid molecule covalently bound with CS via the spacer to the chondroitin sulfate derivative is preferably 3 w/w % or more, more preferably 10 w/w % or more and even more preferably 30 w/w % or more. Furthermore, the content ratio of the steroid molecule can be suitably selected according to such factors as the type of steroid molecule, its properties such as the potency of its effect or solubility in water, and the type of spacer.

The release rate of steroid from the chondroitin sulfate derivative can be suitably selected according to the objective and the like. The steroid release rate is preferably 0.1%/day to 4%/day, more preferably 0.1%/day to 3%/day and even more preferably 0.5%/day to 1%/day in a 10 mM phosphate buffer solution of pH 7.4 and 36° C. Here, steroid release rate refers to the amount of change in the release ratio (%) per day, and is defined as the slope of a graph obtained by plotting time on the horizontal axis and plotting the release ratio (%), which is the ratio of the amount of steroid released (moles) to the total number (100%) of moles of the group derived from a steroid contained in the chondroitin sulfate derivative, on the vertical axis.

Thus, in the case the release rate maintains a constant value during the measurement period, the graph becomes a monotonically increasing straight line. In this case, for example, if all of the steroid contained in the chondroitin sulfate derivative is released in 10 days in a 10 mM phosphate buffer solution of pH 7.4 and 36° C., the release rate is expressed as 10%/day.

On the other hand, in the case the release rate is not constant but rather decreases over time (the graph is convex and demonstrates a gentle, monotonically increasing curve), the change in the release ratio during the initial rise period (for example, three days) is calculated by linear approximation.

Meanwhile, the steroid released amount (amount of steroid released) is measured by a method suitably selected according to the type of steroid.

(2) Method for Producing Chondroitin Sulfate Derivative

The chondroitin sulfate derivative can be obtained by covalently bonding a functional group of the CS molecule (such as a carboxyl group) and a functional group of the steroid (such as a hydroxyl group) via a spacer having a specific structure.

Although the following provides an explanation of an example of a method for producing the chondroitin sulfate derivative, the production method thereof is not limited to the following method.

The chondroitin sulfate derivative obtained by covalently bonding a group derived from CS and a group derived from a steroid via a spacer can be produced by a production method including, for example, the steps indicated below:

(A) covalently bonding a hydroxyl group of a steroid by condensing with a carboxyl group of the spacer-forming molecule (ester bonding), and (B) covalently bonding a carboxyl group of CS by condensing with an amino group of the spacer-forming molecule (amide bonding).

In step (A), a hydroxyl group of the steroid and a carboxyl group of the spacer-forming molecule are condensed to form a covalent bond. At this time, the amino group of the spacer-forming molecule intended to react with CS may be protected as necessary by a commonly used method.

In step (B), a carboxyl group of CS and an amino group of the spacer-forming molecule are condensed to form a covalent bond. At this time, the carboxyl group of the spacer-fanning molecule intended to react with the steroid may be protected as necessary by a commonly used method.

The method for producing the chondroitin sulfate derivative is only required to include step (A) and step (B), and there are no limitations on the order in which these steps are carried out.

The condensation (esterification, amidation) method may be suitably selected from commonly used methods. Examples of condensation methods include a method that uses a condensing agent such as a water-soluble carbodiimide (such as 1-(3-dimethylaminopropyl)-3-ethylcarbodiimide hydrochloride), 4-(4,6-dimethoxy-1,3,5-triazin-2-yl)-4-methylmorpholinium chloride hydrate (DMT-MM) or dicyclohexyl carbodiimide, a symmetric acid anhydride method, a mixed acid anhydride method and an active ester method. Condensation reaction conditions are suitably selected according to the applied condensation reaction.

The spacer-forming molecule is preferably selected so as to obtain a desired steroid release rate. The spacer-forming molecule has a linking group that links two reactive functional groups consisting of a carboxyl group that forms an ester bond with the steroid and an amino group that forms an amide bond with CS. The linking group is preferably selected so as to control the decomposition rate of the ester bond with the steroid. The method for selecting the spacer-forming molecule is, as previously described, selected so as to be able to achieve a desired decomposition rate by suitably combining m and $R^1$.

(3) Pharmaceutical Composition

The pharmaceutical composition contains at least one type of chondroitin sulfate derivative, and may further contain other components such as a pharmaceutically acceptable excipient as necessary. Examples of other components in addition to the pharmaceutically acceptable excipient include a surfactant, physiologically active substance, stabilizer, liquid medium and the like. The physiologically active substance may be the same as or different from the steroid released from the chondroitin sulfate derivative.

There are no particular limitations on the application of the pharmaceutical composition, and is preferably used, for example, for treating bladder diseases.

(4) Agent for Treating Bladder Diseases

The agent for treating bladder diseases is a pharmaceutical composition containing at least one type of chondroitin sulfate derivative that is used to treat bladder diseases.

The term "treat" used in the present specification refers to any form of treatment performed for a disease, and includes cure and improvement of a disease as well as inhibition of the progression thereof (prevention of exacerbation).

Although there are no particular limitations on the form of the agent for treating provided it is in the form of a preparation or pharmaceutical that can be administered to the urinary bladder of human, it is preferably in the form of a liquid at the time of administration, and examples thereof include solutions, suspensions and the like. The solution or suspension can also be administered by preparing a solution or suspension by dissolving a powder of the chondroitin sulfate derivative at the time of use. The agent for treating bladder diseases is preferably used for intravesical administration.

The dosage of the agent for treating bladder diseases is only required to be an amount sufficient for coating the entire mucous membrane inside the urinary bladder, and in humans, for example, is about 5 mL to 200 mL.

The concentration of the chondroitin sulfate derivative in the agent for treating bladder diseases in the case of administering in the form of a liquid is only required to be that which allows passage through a urinary catheter in the case of administering using a urinary catheter, and can be suitably adjusted by a person with ordinary skill in the art.

An example of a method used to administer the agent for treating bladder diseases consists of inserting a urinary catheter into the urinary bladder under aseptic conditions and discharging any residual urine followed by injecting the agent for treating bladder diseases through the same catheter.

After having been injected into the urinary bladder, the agent for treating bladder diseases is thought to enable the gradual release of steroid over a long period of time (for example, one week or longer) as a result of the CS and steroid reaching and adhering to the bladder wall while remaining covalently bonded via the spacer followed by gradual decomposition of the covalent bond between the spacer and steroid.

The agent for treating bladder diseases allows steroid to be gradually released in the urinary bladder. The amount of time during which the steroid is continued to be released in the urinary bladder (retention of effect) is preferably 168 hours (seven days) or more and more preferably 336 hours (14 days) or more.

The intravesical administration frequency of the agent for treating bladder diseases can be determined from the dynamics of the chondroitin sulfate derivative and the steroid released from the chondroitin sulfate derivative. Examples of the administration frequency include, but are not limited to, once per week to once per month.

The objective of the agent for treating bladder diseases is to be applied to the treatment of bladder diseases. The term "Bladder diseases" used in the present specification refers to diseases and any other abnormalities that occur in the urinary bladder, and include, for example, acute cystitis, chronic cystitis, interstitial cystitis, hemorrhagic cystitis, radiation cystitis and overactive bladder. The agent for treating bladder diseases is particularly preferably used for the treatment of interstitial cystitis. The concept of interstitial cystitis may include that referred to as painful bladder syndrome (PBS or bladder pain syndrome (BPS)) and that referred to as hypersensitive bladder syndrome (HBS).

(5) Method for Treating Bladder Diseases

The method for treating bladder diseases includes a step for intravesical administration of the agent for treating bladder diseases. The method for treating bladder diseases may further include other steps as necessary. The method for treating bladder diseases can be carried out in the same manner as that in accordance with the explanation of "(4) Agent for Treating Bladder Diseases" of the previous section, and preferable conditions, administration frequency and the like are the same as previously described.

(6) Urinary Function Ameliorant

The term "urinary function ameliorant" used in the present specification refers to the improvement of micturition and any other abnormalities relating to urinary function. Namely, the urinary function ameliorant is an agent that improves urinary function by intravesical administration of the above-mentioned pharmaceutical composition, and includes the concept of a micturition ameliorant. As will be understood from the examples described hereinafter, since the above-mentioned pharmaceutical composition is able to improve urinary function such as by significantly increasing intercontraction interval or increasing single voided volume, it can also be used to improve chronic micturition characteristic of interstitial cystitis. The urinary function ameliorant can be administered in the same manner as that in accordance with the above-mentioned explanation of the method for treating bladder diseases, and preferable conditions, administration frequency and the like are the same as previously described.

(7) Method for Improving Urinary Function

The method for improving urinary function includes a step for intravesical administration of the urinary function ameliorant. The method for improving urinary function may further include other steps as necessary. The method for improving urinary function can be carried out in the same manner as that in accordance with the explanation of "(6) Urinary Function Ameliorant" of the previous section, and preferable conditions, administration frequency and the like are the same as previously described.

In addition, the present invention includes the following aspects based on the novel finding that, in a compound in which a group derived from CS and a group derived from a steroid are covalently bonded together via a spacer, by selecting and interposing a spacer between these groups that has specific properties (a spacer that lowers the release rate of the steroid from the compound in comparison with the case of using a specific amino acid residue as a spacer in this compound), systemic adverse side effects attributable to the steroid can be reduced.

(8) Another Aspect of Chondroitin Sulfate Derivative

Another aspect of the present invention of the chondroitin sulfate derivative is a compound in which a group derived from CS and a group derived from a steroid are covalently bonded together via a spacer, wherein the spacer exhibits a lower release rate of the steroid from the compound in comparison with the case of using a glycine residue as a spacer in the compound. In particular, a spacer is preferably employed with which the release rate of the steroid from the above-mentioned compound is equal to or lower than the case of using a β-alanine residue as a spacer in the above-mentioned compound.

Here, the spacer molecule in another aspect of the chondroitin sulfate derivative is only required to be a divalent linking group that links both the group derived from CS and the group derived from the steroid, and there are no particular limitations thereon provided the release rate of the steroid from this compound is lower than the case of employing a glycine residue, and preferably a β-alanine residue, as spacer in this compound. A specific example of the spacer includes a divalent linking group represented by general formula (I) described in the above-mentioned section (1) entitled "Chondroitin Sulfate Derivative" and the like.

Here, the release rate of steroid from the above-mentioned compound can be measured using the method described in the previously described section (1) entitled "Chondroitin Sulfate Derivative" or the method described in Test Example A2.

In addition, in order to select the above-mentioned spacer having specific properties, the spacer is determined by dissolving compounds having a specific structure in a 10 mM phosphate buffer solution of pH 7.4 and 36° C. and comparing the values obtained by dividing the steroid release ratio (%) at one week later by 7 and by selecting a compound with which the release rate of steroid from the compound is lower than that of a specific amino acid residue spacer out of these compounds.

By comparing release rates determined in this manner, a spacer can be selected with which the release rate of steroid is lower in comparison with the case in which the spacer is a glycine residue, and preferably a β-alanine residue.

The explanations of the CS, steroid, spacer, covalent bonds and the like that compose another aspect of the chondroitin sulfate derivative, explanations regarding the production of another aspect of the chondroitin sulfate derivative, and the like are the same as described in the previously described sections (1) and (3) to (7) entitled "Chondroitin Sulfate Derivative", "Pharmaceutical Composition", "Agent for Treating Bladder Diseases", "Method for Treating Bladder Diseases", "Urinary Function Ameliorant" and "Method for Improving Urinary Function" provided they do not conflict with matters explained in this other aspect of the chondroitin sulfate derivative.

(9) Another Aspect of Method for Producing Chondroitin Sulfate Derivative

The present invention includes another aspect of the method for producing a chondroitin sulfate derivative as described below. Another aspect of the method for producing a chondroitin sulfate derivative is a method for producing a compound in which a group derived from CS and a group derived from a steroid are covalently bonded together via a spacer, including (C) a step for selecting a spacer with which the release rate of the steroid from the compound is lower in comparison with the case of selecting a glycine residue as a spacer in the compound.

The production method can include a step for covalently bonding a group derived from CS and a group derived from a steroid via the spacer selected according to that described above. There are no particular limitations on the method used to covalently bond the above-mentioned groups, and for example, the selected spacer and the steroid may be condensed by a known method to obtain an intermediate followed by condensing this intermediate with CS using a known method.

For example, the steps (A) and (B) described in the previously described section (2) entitled "Method for Producing Chondroitin Sulfate Derivative" can be included after the above-mentioned step (C). In addition, selection of the spacer in the above-mentioned step (C) is not necessarily required to be carried out continuously with another step, but rather, for example, the spacer may be selected in advance followed by carrying out other subsequent steps at a later date.

Although the following provides a more detailed explanation of other aspects of the production method, the production method is not limited thereto.

a) A method for producing a compound in which a group derived from CS and a group derived from a steroid are covalently bonded together via a spacer, including at least following steps 1 and 2:

step 1: selecting a spacer with which the release rate of the steroid from the compound is lower in comparison with the case of selecting a glycine residue (and more preferably, β-alanine residue) as a spacer in the compound; and step 2: covalently bonding the group derived from CS and the group derived from the steroid via the spacer selected in step 1.

b) A method for producing a compound in which a group derived from CS and a group derived from a steroid are covalently bonded together via a spacer, including at least following steps 1 to 3:

step 1: selecting a spacer with which the release rate of the steroid from the compound is lower in comparison with the case of selecting a glycine residue (and more preferably a β-alanine residue) as a spacer;

step 2: obtaining an intermediate by covalently bonding (such as ester bonding) the spacer selected in step 1 with the steroid; and step 3: covalently bonding (such as amide bonding) the intermediate obtained in step 2 with CS.

In addition, the production method may also be the production method of the "Pharmaceutical Composition", "Agent for Treating Bladder Diseases" and "Urinary Function Ameliorant" and the like described in the previously described sections (3), (4) and (6). In this case, a step for adding pharmaceutically acceptable components according to the object of production (pharmaceutical composition, agent for treating bladder diseases or urinary function ameliorant) can be further included.

The explanations of CS, steroid, spacer, covalent bonds and the like in the production method as well as other explanations relating to production are the same as described in the previously described section (2) entitled "Method for Producing Chondroitin Sulfate Derivative" provided they do not conflict with matters explained in the production method of the present invention.

In this manner, in a compound in which a group derived from CS and a group derived from a steroid are covalently bonded together via a spacer, by selecting and interposing a spacer with which the release rate of the steroid from this compound can be lowered in comparison with the case of using a specific amino acid residue as a spacer in this compound, a compound, pharmaceutical composition, agent for treating bladder diseases and/or urinary function ameliorant can be obtained in which systemic adverse side effects attributable to the steroid are reduced. The production method is useful for producing these products in which adverse side effects have been reduced.

EXAMPLES

The following provides a more detailed explanation of examples and test examples of the present invention. However, the technical scope of the present invention is not limited thereby. Meanwhile, the steroid content (w/w %) of a chondroitin sulfate derivative was measured by a method described hereinafter.

Example 1

Preparation of CS Introduced with 21-β-Alanyl-Prednisolone (1-1) Preparation of 21-(Boc-β-Alanyl)-Prednisolone 1.58 g of Boc-β-alanine (Watanabe Chemical Industries, Ltd.) were dissolved in 60 mL of dichloromethane and 20 mL of dimethylformamide followed by the addition of 3.00 g of prednisolone (Wako Pure Chemical Industries, Ltd., abbreviated as "PRED") and 305 mg of 4-dimethylaminopyridine (Wako Pure Chemical Industries, Ltd.) and dissolving therein. Subsequently, 4.00 g of water-soluble carbodiimide (Tokyo Chemical Industry Co., Ltd.) were added while cooling with ice followed by stirring overnight at room temperature. After confirming disappearance of the raw material by thin layer chromatography, saturated aqueous ammonium chloride solution was added while cooling with ice to stop the reaction. Extraction and phase separation was then carried out using dichloromethane, toluene and water and the collected organic layers were sequentially washed with saturated aqueous ammonium chloride solution, saturated aqueous sodium bicarbonate solution and saturated aqueous sodium chloride solution. Subsequently, after dehydrating with magnesium sulfate and filtering, the solvent was distilled off under reduced pressure. After dissolving the concentrate with chloroform, the solvent was again distilled off under reduced pressure. This procedure was repeated three times to obtain 4.73 g of desired 21-(Boc-β-alanyl)-prednisolone (Compound 1) (yield: 107%).

(1-2) Preparation of 21-β-Alanyl-Prednisolone Hydrochloride 4.73 g of Compound 1 obtained in (1-1) were dissolved in 90 mL of dichloromethane followed by the addition of 45 mL of 4 M hydrochloric acid/ethyl acetate (Watanabe Chemical Industries, Ltd.) while cooling with ice and stirring for 3 hours. After confirming disappearance of the raw material by thin layer chromatography, the solvent was distilled off under reduced pressure. After washing the concentrate with diethyl ether, the solvent was distilled off under reduced pressure to obtain 3.42 g of desired 21-β-alanyl-prednisolone hydrochloride (Compound 2) (yield: 88%).

(1-3) Preparation of CS Introduced with 21-β-Alanyl-Prednisolone 524 mg of CS (sodium salt, Seikagaku Corporation, weight average molecular weight: approx. 20,000, determined by light scattering) were dissolved in 10 mL of distilled water followed by the addition of 10 mL of acetone and stirring. 395 mg of Compound 2 obtained in (1-2) and 838 mg of 4-(4,6-dimethoxy-1,3,5-triazin-2-yl)-4-methylmorpholinium chloride hydrate (abbreviated as DMT-MM, Tokuyama Corporation) were added while washing with a total of 3 mL of 50% acetone/distilled water followed by stirring overnight. Subsequently, a reaction solution obtained by adding 0.1 g of sodium chloride and the 50% acetone/distilled water of the washings and dissolving the sodium chloride was sequentially added to 300 mL of 90% ethanol/distilled water to form a precipitate followed by centrifuging and discarding the supernatant. Subsequently, the precipitate was sequentially washed with 90% ethanol/distilled water and 95% ethanol/distilled water. The resulting precipitate was then dried overnight under reduced pressure to obtain 787 mg of desired CS introduced with 21-β-alanyl-prednisolone. The content (w/w %) of prednisolone introduced into the CS was determined to be 35 w/w % as a result of measuring absorbance at 248 nm.

Example 2

Preparation of CS Introduced with 21-β-Alanyl-Betamethasone (2-1) Preparation of 21-(Boc-β-Alanyl)-Betamethasone 2.0 g of Boc-β-alanine were dissolved in 50 mL of dichloromethane and 50 mL of dimethylformamide followed by the addition of 4.15 g of betamethasone (Wako Pure Chemical Industries, Ltd., abbreviated as "BTM"). Subsequently, 389 mg of 4-dimethylaminopyridine and 2.64 g of water-soluble carbodiimide were added while cooling with ice followed by stirring overnight at room temperature. After confirming disappearance of the raw material by thin layer chromatography, saturated aqueous ammonium chloride solution was added to stop the reaction. Extraction and phase separation was then carried out using toluene and water and the collected organic layers were sequentially washed with saturated aqueous ammonium chloride solution, saturated aqueous sodium bicarbonate solution and saturated aqueous sodium chloride solution. Subsequently, after dehydrating with magnesium sulfate and filtering, the solvent was distilled off under reduced pressure to obtain 5.84 g of desired 21-(Boc-β-alanyl)-betamethasone (Compound 3) (yield: 98%).

(2-2) Preparation of 21-β-Alanyl-Betamethasone Hydrochloride 5.84 g of Compound 3 obtained in (2-1) were dissolved in 120 mL of tetrahydrofuran followed by the addition of 100 mL of 4 M hydrochloric acid/ethyl acetate while cooling with ice and stirring for 3 hours at room temperature. After confirming disappearance of the raw material by thin layer chromatography, the solvent was distilled off under reduced pressure. After washing the concentrate with diethyl ether and filtering, the solvent was distilled off under reduced pressure to obtain 4.60 g of desired 21-β-alanyl-betamethasone hydrochloride (Compound 4) (yield: 96%).

(2-3) Preparation of CS Introduced with 21-β-Alanyl-Betamethasone 10 mL of distilled water were added to 524 mg of CS (sodium salt, weight average molecular weight: approx. 20,000) to dissolve the CS followed by the addition of 10 mL of acetone and stirring. 422 mg of Compound 4 obtained in (2-2) and 839 mg of DMT-MM were added while washing with a total of 3 mL of 50% acetone/distilled water followed by stirring overnight. Subsequently, a reaction solution obtained by adding 0.1 g of sodium chloride and the 50% acetone/distilled water of the washings and dissolving the sodium chloride was sequentially added to 300 mL of 90% ethanol/distilled water to form a precipitate followed by centrifuging and discarding the supernatant. Subsequently, the precipitate was sequentially washed with 90% ethanol/distilled water and 95% ethanol/distilled water. The resulting precipitate was then dried overnight under reduced pressure to obtain 770 mg of desired CS introduced with 21-β-alanyl-betamethasone. The content (w/w %) of betamethasone introduced into the CS was determined to be 40 w/w % as a result of measuring absorbance at 242 nm.

Example 3

Preparation of CS Introduced with 21-β-Alanyl-Triamcinolone Acetonide (3-1) Preparation of 21-(Boc-β-Alanyl)-Triamcinolone Acetonide 2.63 g of Boc-β-alanine were dissolved in 40 mL of dichloromethane and 10 mL of dimethylformamide followed by the addition of 5.01 g of triamcinolone acetonide (Wako Pure Chemical Industries, Ltd., abbreviated as "TA"). Subsequently, 426 mg of 4-dimethylaminopyridine and 3.32 g of water-soluble carbodiimide were added while cooling with ice followed by stirring overnight at room temperature. After confirming disappearance of the raw material by thin layer chromatography, saturated aqueous ammonium chloride solution was added to stop the reaction. Extraction and phase separation was then carried out using toluene and water and the collected organic layers were sequentially washed with saturated aqueous ammonium chloride solution, saturated aqueous sodium bicarbonate solution and saturated aqueous sodium chloride solution. Subsequently, after drying with magnesium sulfate and filtering, the solvent was distilled off under reduced pressure to obtain 6.66 g of desired 21-(Boc-β-alanyl)-triamcinolone acetonide (Compound 5) (yield: 96%).

(3-2) Preparation of 21-β-Alanyl-Triamcinolone Acetonide Hydrochloride 6.66 g of Compound 5 obtained in (3-1) were dissolved in 90 mL of tetrahydrofuran followed by the addition of 90 mL of 4 M hydrochloric acid/ethyl acetate while cooling with ice and stirring for 3 hours at room temperature. After confirming disappearance of the raw material by thin layer chromatography, the solvent was distilled off under reduced pressure. After washing the concentrate with diethyl ether, the solvent was distilled off under reduced pressure to obtain 5.78 g of desired 21-β-alanyl-triamcinolone acetonide hydrochloride (Compound 6) (yield: 97%).

(3-3) Preparation of CS Introduced with 21-β-Alanyl-Triamcinolone Acetonide 524 mg of CS (sodium salt, weight average molecular weight: approx. 20,000) were dissolved in 10 mL of distilled water followed by the addition of 10 mL of acetone and stirring. 458 mg of Compound 6 obtained in (3-2) and 839 mg of DMT-MM were added while washing with a total of 3 mL of 50% acetone/distilled water followed by stirring overnight. Subsequently, a reaction solution obtained by adding 0.1 g of sodium chloride and the 50% acetone/distilled water of the washings and dissolving the sodium chloride was sequentially added to 300 mL of 90% ethanol/distilled water to form a precipitate followed by centrifuging and discarding the supernatant.

Subsequently, the precipitate was sequentially washed with 90% ethanol/distilled water and 95% ethanol/distilled water. The resulting precipitate was then dried overnight under reduced pressure to obtain 819 mg of desired CS introduced with 21-β-alanyl-triamcinolone acetonide. The content (w/w %) of triamcinolone acetonide introduced into the CS was determined to be 38 w/w % as a result of measuring absorbance at 242 nm.

Example 4

Preparation of CS Introduced with 21-Glycyl-Triamcinolone Acetonide (4-1) Preparation of 21-(Boc-Glycyl)-Triamcinolone Acetonide 1.71 g of Boc-glycine (Watanabe Chemical Industries, Ltd.) were dissolved in 30 mL of dichloromethane and 10 mL of dimethylformamide followed by the addition of 4.01 g of triamcinolone acetonide. Subsequently, 338 mg of 4-dimethylaminopyridine and 2.65 g of water-soluble carbodiimide were added while cooling with ice followed by stirring overnight at room temperature. After confirming disappearance of the raw material by thin layer chromatography, saturated aqueous ammonium chloride solution was added to stop the reaction. Extraction and phase separation was then carried out using toluene and water and the collected organic layers were sequentially washed with saturated aqueous ammonium chloride solution, saturated aqueous sodium bicarbonate solution and saturated aqueous sodium chloride solution. Subsequently, after dehydrating with magnesium sulfate and filtering, the solvent was distilled off under reduced pressure to obtain 5.21 g of desired 21-(Boc-glycyl)-triamcinolone acetonide (Compound 7) (yield: 96%).

(4-2) Preparation of 21-Glycyl-Triamcinolone Acetonide Hydrochloride 5.21 g of Compound 7 obtained in (4-1) were dissolved in 90 mL of tetrahydrofuran followed by the addition of 90 mL of 4 M hydrochloric acid/ethyl acetate while cooling with ice and stirring for 3 hours. After confirming disappearance of the raw material by thin layer chromatography, the solvent was distilled off under reduced pressure. After washing the concentrate with diethyl ether, the solvent was distilled off under reduced pressure to obtain 4.16 g of desired 21-glycyl-triamcinolone acetonide hydrochloride (Compound 8) (yield: 88%).

(4-3) Preparation of CS Introduced with 21-Glycyl-Triamcinolone Acetonide 1.04 g of CS (sodium salt, weight average molecular weight: approx. 20,000) were dissolved in 20 mL of distilled water followed by the addition of 20 mL of acetone and stirring. 806 mg of Compound 8 obtained in (4-2) and 1.46 g of DMT-MM were added while washing with a total of 20 mL of 50% acetone/distilled water followed by stirring overnight. Subsequently, a reaction solution obtained by adding 4 g of sodium chloride and the 50% acetone/distilled water of the washings and dissolving the sodium chloride was added to 420 mL of ethanol to form a precipitate followed by centrifuging and discarding the supernatant.

Subsequently, the precipitate was sequentially washed with 80% ethanol/distilled water, 90% ethanol/distilled water, 95% ethanol/distilled water and ethanol. The resulting precipitate was then dried overnight under reduced pressure to obtain 1.34 g of desired CS introduced with 21-glycyl-triamcinolone acetonide. The content (w/w %) of triamcinolone acetonide introduced into the CS was determined to be 37 w/w % as a result of measuring absorbance at 241 nm.

Example 5

Preparation of CS Introduced with 21-Isoleucyl-Triamcinolone Acetonide (5-1) Preparation of 21-(Boc-Isoleucyl)-Triamcinolone Acetonide 2.24 g of Boc-isoleucine (Watanabe Chemical Industries, Ltd.) were dissolved in 30 mL of dichloromethane and 10 mL of dimethylformamide followed by the addition of 4.00 g of triamcinolone acetonide. Subsequently, 338 mg of 4-dimethylaminopyridine and 2.65 g of water-soluble carbodiimide were added while cooling with ice followed by stirring overnight at room temperature. After confirming disappearance of the raw material by thin layer chromatography, saturated aqueous ammonium chloride solution was added to stop the reaction. Extraction and phase separation was then carried out using toluene and water and the collected organic layers were sequentially washed with saturated aqueous ammonium chloride solution, saturated aqueous sodium bicarbonate solution and saturated aqueous sodium chloride solution. Subsequently, after dehydrating with magnesium sulfate and filtering, the solvent was distilled off under reduced pressure to obtain 5.65 g of desired 21-(Boc-isoleucyl)-triamcinolone acetonide (Compound 9) (yield: 95%).

(5-2) Preparation of 21-Isoleucyl-Triamcinolone Acetonide Hydrochloride 5.65 g of Compound 9 obtained in (5-1) were dissolved in 90 mL of tetrahydrofuran followed by the addition of 90 mL of 4 M hydrochloric acid/ethyl acetate while cooling with ice and stirring for 3 hours at room temperature. After confirming disappearance of the raw material by thin layer chromatography, the solvent was distilled off under reduced pressure. After washing the concentrate with diethyl ether, the solvent was distilled off under reduced pressure to obtain 3.05 g of desired 21-isoleucyl-triamcinolone acetonide hydrochloride (Compound 10) (yield: 60%).

(5-3) Preparation of CS Introduced with 21-Isoleucyl-Triamcinolone Acetonide 1.04 g of CS (sodium salt, weight average molecular weight: approx. 20,000) were dissolved in 20 mL of distilled water followed by the addition of 20 mL of acetone and stirring. 881 mg of Compound 10 obtained in (5-2) and 1.46 g of DMT-MM were added while washing with a total of 34 mL of 50% acetone/distilled water followed by stirring overnight. Subsequently, a reaction solution obtained by adding 5 g of sodium chloride and the 50% acetone/distilled water of the washings and dissolving the sodium chloride was sequentially added to 444 mL of ethanol to form a precipitate followed by discarding the supernatant. The precipitate was then washed with 80% ethanol/distilled water followed by discarding the supernatant. 95% ethanol/distilled water was added followed by filtering with a filter. Precipitate remaining on the filter was sequentially washed with 95% ethanol/distilled water and ethanol and the resulting precipitate was then dried overnight under reduced pressure to obtain 1.59 g of desired CS introduced with 21-isoleucyl-triamcinolone acetonide. The content (w/w %) of triamcinolone acetonide introduced into the CS was determined to be 35 w/w % as a result of measuring absorbance at 241 nm.

<Measurement of Steroid Content>

Each of the resulting compounds described above was suitably dissolved and diluted using distilled water within the range over which absorbance demonstrates linearity. Absorbance in the vicinity of the maximum absorption wavelength of the measurement target was measured with a UV-visible spectrophotometer (Shimadzu Corporation).

The content (w/w %) of steroid introduced into each compound was calculated using the calculation formula indicated below.

Steroid content (w/w %)=(Abs/ε×MwST)/((WT× (100−WD)/100)/(V×Mc))×100

Abs: Absorbance
WT: Sample weight (mg)
WD: Sample weight reduction on drying (%)
ε: Molar extinction coefficient
MwST: Steroid molecular weight
V: Solution volume (mL)
Mc: Dilution factor The molar extinction coefficients were calculated from Compounds 2, 4, 6, 8 and 10 synthesized in compliance with the methods described in Examples 1 to 5. The molar extinction coefficients (ε) and molecular weights of the steroids used (MwST) of each compound are shown in Table 1.

TABLE 1

| Compound | ε | MwST |
| --- | --- | --- |
| 21-β-Alanyl-Prednisolone Hydrochloride | 13525 | 360.4 |
| 21-β-Alanyl-Betamethasone Hydrochloride | 13402 | 392.5 |
| 21-β-Alanyl-Triamcinolone Acetonide Hydrochloride | 14478 | 434.5 |
| 21-Glycyl-Triamcinolone Acetonide Hydrochloride | 14730 | 434.5 |
| 21-Isoleucyl-Triamcinolone Acetonide Hydrochloride | 14292 | 434.5 |

The names of the synthesized chondroitin sulfate derivatives used in the following examples are abbreviated as indicated below.

TABLE 2

| Compound (Chondroitin Sulfate Derivative) | Abbreviation |
| --- | --- |
| CS introduced with 21-β-Alanyl-Prednisolone | CS-βAla-PRED |
| CS introduced with 21-β-Alanyl-Betamethasone | CS-βAla-BTM |
| CS introduced with 21-β-Alanyl-Triamcinolone Acetonide | CS-βAla-TA |
| CS introduced with 21-Glycyl-Triamcinolone Acetonide | CS-Gly-TA |
| CS introduced with 21-Isoleucyl-Triamcinolone Acetonide | CS-Ile-TA |

<Drug Release Test>

The release ratio of drug (steroid) from the chondroitin sulfate derivative was evaluated in the manner indicated below for examples used in a drug release test.

(1) Preparation of Phosphate Buffer Solution 780 mg (5.0 mmol) of sodium dihydrogen phosphate dihydrate were dissolved in 500 mL of distilled water to prepare a Solution A. Separate therefrom, 1.79 g (5.0 mmol) of sodium hydrogen phosphate dodecahydrate were dissolved in 500 mL of distilled water to prepare a Solution B. Solution A and Solution B were mixed at a ratio of 3:7 to prepare a phosphate buffer solution of pH 7.4.

(2) Preparation of Borate Buffer Solution 0.62 g (10 mmol) of boric acid and 0.75 g (10 mmol) of potassium chloride were weighed out and dissolved in 500 mL of distilled water to prepare a Solution 1. Separate therefrom, a 0.1 M sodium hydroxide solution was diluted 10-fold with distilled water to prepare a Solution 2. 50 mL of Solution 1 and 7 mL of Solution 2 were added to a 100 mL volumetric flask and brought to a volume of 100 mL with distilled water to prepare a borate buffer solution of pH 8.0.

(3) Evaluation Method

After dissolving the chondroitin sulfate derivatives obtained in the examples in each of the buffer solutions having respective pH values to a concentration of 5 mg/10 mL, the resulting solutions were kept for 1 week in a constant temperature bath at 36° C. followed by evaluating the drug release ratio during that time every 24 hours by high-performance liquid chromatography (HPLC).

The drug release ratios were evaluated by measuring the ratio of the amount of drug remaining in the chondroitin sulfate derivatives and the amount of drug released using a size exclusion chromatograph (TSKgel α, Tosoh Corporation).

The conditions used during high-performance liquid chromatography are described in detail below.

Analysis time: 40 min
Flow rate: 0.5 mL/min
Gradient: Isocratic
Eluent: Acetonitrile (for HPLC):physiological saline=1:2
Detector: UV detector (240 nm)
Temperature: 36° C.

<Test Example A1> Change in Release Characteristics due to Difference in Type of Drug Drug release ratio (%) for a period of 1 week at 36° C. was evaluated by HPLC for CSβAla-PRED, CS-βAla-BTM and CS-βAla-TA prepared in compliance with the methods of Examples 1, 2 and 3. The drug release ratios were evaluated every 24 hours. The results are shown in the table below.

TABLE 3

| Elapsed | CS-βAla-PRED | | CS-βAla-BTM | | CS-βAla-TA | |
|---|---|---|---|---|---|---|
| Time (days) | pH 7.4 | pH 8.0 | pH 7.4 | pH 8.0 | pH 7.4 | pH 8.0 |
| 0 | 0.6% | 0.6% | 0.5% | 0.6% | 1.3% | 1.3% |
| 1 | 3.5% | 7.0% | 1.2% | 2.9% | 1.9% | 2.7% |
| 2 | 5.6% | 12.5% | 1.7% | 4.8% | 3.2% | 4.2% |
| 3 | 7.8% | 17.8% | 2.4% | 6.7% | 3.7% | 5.7% |
| 4 | 10.0% | 22.5% | 3.2% | 9.4% | 4.5% | 7.4% |
| 5 | 12.0% | 27.3% | 3.8% | 11.4% | 5.0% | 8.6% |
| 6 | 14.3% | 31.6% | 4.4% | 13.2% | 5.9% | 10.0% |
| 7 | 16.2% | 35.1% | 5.0 | 15.0% | 6.7% | 11.3% |
| Release Rate (%/day) | 2.2% | 4.9% | 0.7% | 2.1% | 0.8% | 1.4% |

Among the release rates for CS-βAla-PRED, CS-βAla-BTM and CS-βAla-TA, CS-βAla-PRED demonstrated the highest release rate both in the case of pH 7.4 and pH 8.0, while the release rates for CS-βAla-BTM and CS-βAla-TA were roughly equal.

<Test Example A-2> Changes in Release Characteristics Due to Difference in Spacer Drug release ratio (%) for a period of 1 week at 36° C. was evaluated by HPLC for CS-βAla-TA, CS-Gly-TA and CS-Ile-TA prepared in compliance with the methods of Examples 3, 4 and 5. The drug release ratios were evaluated every 24 hours. The results are shown in the table below.

TABLE 4

| Elapsed | CS-βAla-TA | | CS-Gly-TA | | CS-Ile-TA | |
|---|---|---|---|---|---|---|
| Time (days) | pH 7.4 | pH 8.0 | pH 7.4 | pH 8.0 | pH 7.4 | pH 8.0 |
| 0 | 0.0% | 0.0% | 0.0% | 0.0% | 0.0% | 0.0% |
| 1 | 0.4% | 1.0% | 5.3% | 13.1% | 0.1% | 0.3% |
| 2 | 0.7% | 2.4% | 10.1% | 23.2% | 0.2% | 0.5% |
| 3 | 1.3% | 3.7% | 15.0% | 32.0% | 0.3% | 0.7% |
| 4 | 1.8% | 5.0% | 19.4% | 39.0% | 0.4% | 1.1% |
| 5 | 2.3% | 6.4% | 23.8% | 44.7% | 0.6% | 1.4% |
| 6 | 2.8% | 7.8% | 28.0% | 49.2% | 0.8% | 1.8% |
| 7 | 3.4% | 9.0% | 31.5% | 53.9% | 0.7% | 2.1% |
| Release Rate (%/day) | 0.5% | 1.3% | 4.5% | 10.6% | 0.1% | 0.3% |

Among the release rates for CS-βAla-TA, CS-Gly-TA and CS-Ile-TA, release rate was the highest for CS-Gly-TA followed by CS-βAla-TA and CS-Ile-TA in that order both in the case of pH 7.4 and pH 8.0.

<In Vivo Evaluation>

<Test Example B1> Evaluation of Urinary Function for CS-Steroid Compounds Using a Rat Hydrochloric Acid-Induced Micturition Model (Steroid Comparison)

Purpose

This study was conducted for the purpose of evaluating the effect of chondroitin sulfate derivatives having different steroids (CS-βAla-PRED, CS-βAla-BTM and CS-βAla-TA) on urinary function following single-dose administration thereof into the bladders of hydrochloric acid-induced micturition model rats.

Method

Chondroitin sulfate derivatives prepared in compliance with the methods of Examples 1, 2 and 3 were dissolved in phosphate-buffered saline to prepare the test substances indicated below.

Test Substances:
(1) Saline (control)
(2) 1.5% (w/v %) CS-βAla-PRED (PRED content: 35 w/w %)
(3) 1.5% (w/v %) CS-βAla-BTM (BTM content: 40 w/w %)
(4) 1.5% (w/v %) CS-βAla-TA (TA content: 38 w/w %)

Rats (SD strain (SPF), females, age 11 to 13 weeks) were laparotomized under pentobarbital general anesthesia (40 mg/kg, i.p.) followed by incising the dome of the bladder and inserting a catheter (PE50) to construct a bladder fistula.

Cystitis was induced using 0.4 M hydrochloric acid. The rats were anesthetized and restrained in Bollman cages seven days after construction of the bladder fistula followed by connecting a urinary catheter, pressure transducer and syringe connected to a syringe pump in parallel. Normal intravesical pressure was measured while continuously infusing physiological saline (3 mL/h). 0.4 M hydrochloric acid was then continuously infused into the bladder for 15 minutes (3 mL/h) to induce micturition.

Two days after continuous instillation of hydrochloric acid, 0.2 mL of each test substance were administered transurethrally using a catheter (PE50) and retained in the bladder for 30 minutes under anesthesia.

Seven days after intravesical instillation of hydrochloric acid, the rats were restrained in Bollman cages followed by connecting a urinary catheter, pressure transducer and syringe connected to a syringe pump in parallel. Changes in intravesical pressure were measured while continuously infusing physiological saline (3 mL/h) starting 20 minutes after the animals emerged from anesthesia. Urinary function was evaluated by measuring intercontraction interval and single voided volume after changes in intravesical pressure had stabilized.

Figure 1:
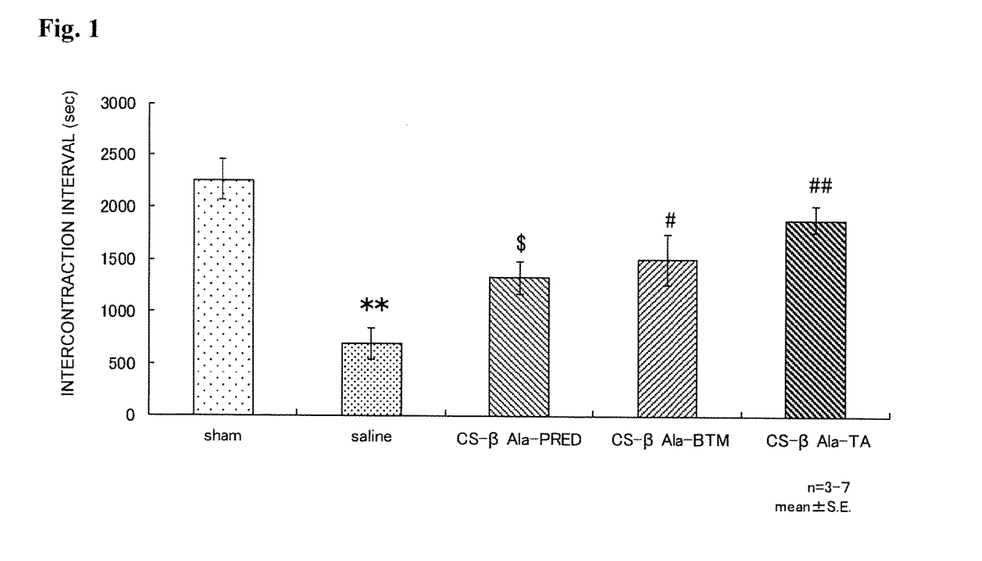
FIG. 1 is a graph indicating the effect of CS-β-alanyl-prednisolone, CS-β-alanyl-betamethasone and CS-β-alanyl-triamcinolone acetonide on intercontraction interval in a rat hydrochloric acid-induced micturition model.

The results are shown in FIG. 1.

Results

The results in FIG. 1 are indicated as average intercontraction interval±standard error (number of animals in each group: 3 to 7). In addition, double asterisks (**) indicate a level of significance of p<0.01 (vs. sham) according to the t-test. A double hash mark (##) indicates a level of significance of p<0.01 (vs. control) according to Dunnett's multiple comparison test, while a single hash mark (#) indicates a level of significance of p<0.05 (vs. control) according to Dunnett's multiple comparison test. A dollar sign ($) indicates a level of significance of p<0.05 (vs. control) according to the t-test.

According to FIG. 1, the CS-βAla-PRED administered group, CS-βAla-BTM administered group and CS-βAla-TA administered group each demonstrated effect that significantly increased intercontraction interval in comparison with the control group. Similarly, with respect to single voided volume, the CS-βAla-PRED administered group, CS-βAla-BTM administered group and CS-βAla-TA administered group each induced a significant increase in single voided volume in comparison with the control group.

Discussion

Since CS-βAla-PRED, CS-βAla-BTM and CS-βAla-TA clearly demonstrated effect that improves urinary function following intravesical administration thereof, compounds in which CS and a steroid are covalently bonded together via a spacer were determined to be effective regardless of the type of steroid.

<Test Example B2> Evaluation of Urinary Function for CS-Steroid Compounds Using a Rat Hydrochloric Acid-Induced Micturition Model (Spacer Comparison)

Purpose

This study was conducted for the purpose of evaluating the effect of chondroitin sulfate derivatives having different spacers (CS-βAla-TA, CS-Gly-TA and CS-Ile-TA) on urinary function following single-dose administration thereof into the urinary bladders of hydrochloric acid-induced micturition model rats.

Method

Chondroitin sulfate derivatives prepared in compliance with the methods of Examples 3, 4 and 5 were dissolved in phosphate-buffered saline to prepare the test substances indicated below.

Test Substances:
(1) Saline (control)
(2) 1.5% (w/v %) CS-βAla-TA (TA content: 37 w/w %)
(3) 1.5% (w/v %) CS-Gly-TA (TA content: 37 w/w %)
(4) 1.5% (w/v %) CS-Ile-TA (TA content: 35 w/w %)

Rats (SD strain (SPF), females, age 11 to 14 weeks) were laparotomized under anesthesia using a mixture of three anesthetic agents (Domitor, Dormicum and Vetorphale at 0.15, 2.0 and 2.5 mg/2.5 mL, respectively, and 0.5 mL/rat, i.v.) followed by incising the dome of the bladder and inserting a catheter (PE50) to construct a bladder fistula.

Cystitis was induced using 0.4 M hydrochloric acid. The rats were anesthetized and restrained in Bollman cages seven days after construction of the bladder fistula followed by connecting a urinary catheter, pressure transducer and syringe connected to a syringe pump in parallel. Normal intravesical pressure was measured while continuously infusing physiological saline (3 mL/h). 0.4 M hydrochloric acid was then continuously infused into the bladder for 15 minutes (3 mL/h) to induce micturition.

Two days after continuous instillation of hydrochloric acid, 0.2 mL of each test substance were administered transurethrally using a catheter (PE50) and retained in the bladder for 30 minutes under anesthesia.

Seven days after intravesical instillation of hydrochloric acid, the rats were restrained in Bollman cages followed by connecting a urinary catheter, pressure transducer and syringe connected to a syringe pump in parallel. Changes in intravesical pressure were measured while continuously infusing physiological saline (3 mL/h) starting 20 minutes after the animals emerged from anesthesia. Intercontraction interval and single voided volume were measured after changes in intravesical pressure had stabilized.

Figure 2:
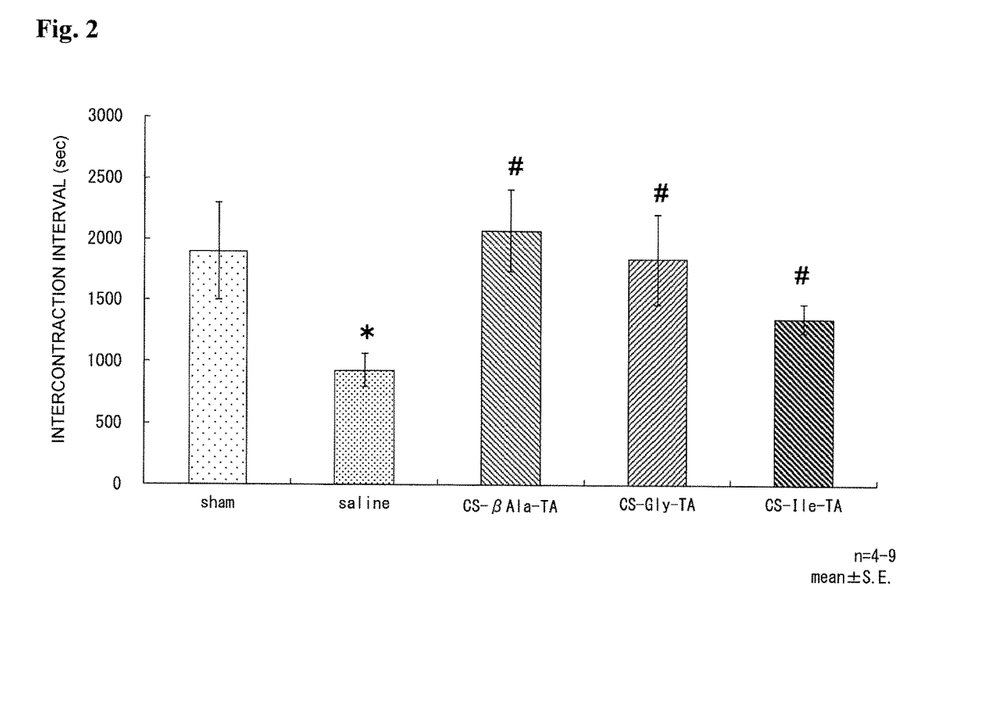
FIG. 2 is a graph indicating the effect of CS-β-alanyl-triamcinolone acetonide, CS-glycyl-triamcinolone acetonide and CS-isoleucyl-triamcinolone acetonide on intercontraction interval in a rat hydrochloric acid-induced micturition model.

The results are shown in FIG. 2.

Body weight changes were determined by measuring body weight four times, namely before surgery, after surgery and immediately before the induction with hydrochloric acid, immediately before administering the test substance (before agent administration), and immediately before measurement of intravesical pressure (cystometry), and are indicated as relative values based on a value of 100% for the body weight prior to surgery for each animal.

Figure 3:
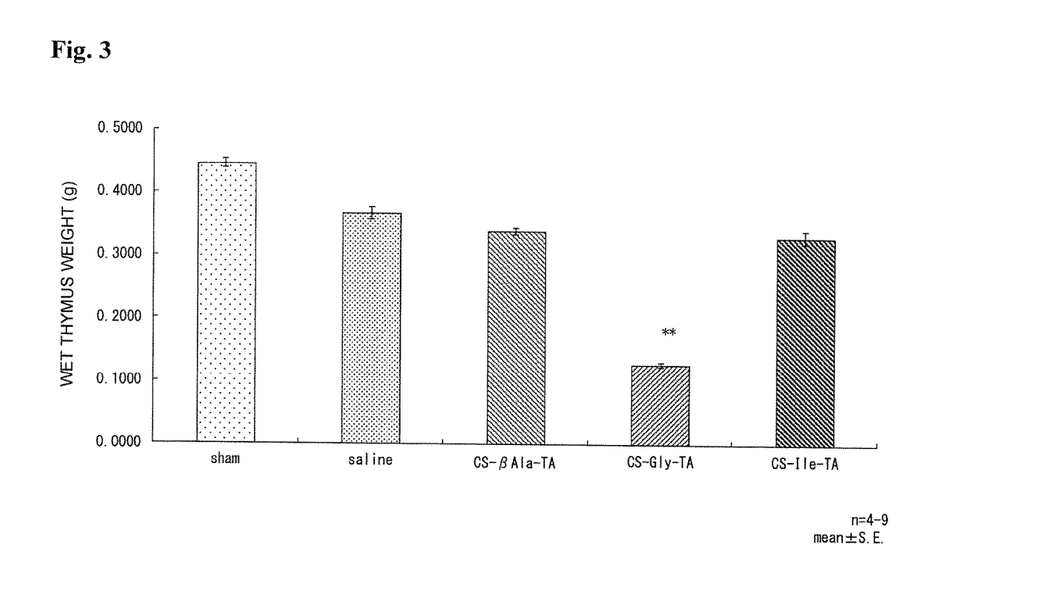
FIG. 3 is a graph indicating the effect of CSβ-alanyl-triamcinolone acetonide, CS-glycyl-triamcinolone acetonide and CS-isoleucyl-triamcinolone acetonide on wet thymus weight in a rat hydrochloric acid-induced micturition model.

In addition, wet thymus weight was determined by collecting a sample of the thymus from euthanized rats following measurement of intravesical pressure (cystometry) and measuring the weight thereof. Weight changes are shown in Table 5 while wet thymus weights are shown in FIG. 3.

TABLE 5

| Group | No. of Animals | Before Surgery (%) | Before induction with hydrochloric acid (%) | Before agent administration (%) | Before cystometry (%) |
|---|---|---|---|---|---|
| Sham | 4 | 100.0 ± 0.0 | 99.9 ± 2.8 | 101.0 ± 2.2 | 103.8 ± 3.0 |
| Saline | 7 | 100.0 ± 0.0 | 99.8 ± 0.7 | 94.5 ± 1.4 | 99.0 ± 1.1 |
| CS-βAla-TA | 9 | 100.0 ± 0.0 | 100.8 ± 1.1 | 96.9 ± 1.3 | 97.8 ± 1.5 |
| CS-Gly-TA | 8 | 100.0 ± 0.0 | 101.4 ± 0.7 | 96.7 ± 1.2 | 89.0 ± 1.7 |
| CS-Ile-TA | 7 | 100.0 ± 0.0 | 98.9 ± 1.3 | 95.7 ± 1.6 | 99.6 ± 1.2 |

Mean ± standard error (number of animals per group: 4 to 9)

Results

The results in FIG. 2 are indicated as average intercontraction interval±standard error (number of animals in each group: 4 to 9). In addition, a single asterisk (*) indicates a level of significance of p<0.05 (vs. sham) according to the t-test. A single hash mark (#) indicates a level of significance of p<0.05 (vs. control) according to the t-test. In addition, in FIG. 3, double asterisks (**) indicate a level of significance of p<0.01 (vs. control) according to the t-test.

According to FIG. 2, the CS-βAla-TA administered group, CS-Gly-TA administered group and CS-Ile-TA administered group each demonstrated effect that significantly increased intercontraction interval in comparison with the control group. Similarly, with respect to single voided volume, the CS-βAla-TA administered group, CS-Gly-TA administered group and CS-Ile-TA administered group each induced a significant increase in single voided volume in comparison with the control group.

On the basis of these results, pharmacological efficacy was determined to be demonstrated even if Ile is used for the spacer-forming molecule. CS-βAla-TA was also determined to demonstrate pharmacological efficacy with favorable reproducibility.

According to FIG. 3, significant decreases in wet thymus weight were not observed in comparison with the control group in the CS-βAla-TA administered group and CS-Ile-TA administered group, and significant decreases in wet thymus weight were only observed in the CS-Gly-TA administered group.

In addition, according to Table 5, weight loss was not observed in comparison with prior to agent administration in the CS-βAla-TA administered group and CS-Ile-TA administered group, and prominent weight loss was only observed in the CS-Gly-TA administered group.

Discussion

CS-βAla-TA, CS-Gly-TA and CS-Ile-TA clearly demonstrated effect that improves urinary function following intravesical administration thereof. However, adverse side effects consisting of decreased wet thymus weight and weight loss were observed for CS-Gly-TA that has a rapid drug release rate, and is clearly unsuitable for intravesical administration. On the other hand, systemic adverse side effects attributable to steroids were clearly determined to be able to be reduced by controlling drug release rate using a space-forming molecule such as βAla or Ile.

<Test Example B3> Evaluation of Urinary Function for CS-Steroid Compounds Using a Rat Hydrochloric Acid-Induced Micturition Model (Comparison of Conjugates and Mixture)

Purpose

This study was conducted for the purpose of evaluating the effect of chondroitin sulfate derivatives during single-dose administration of CS-βAla-BTM and a mixture of CS and betamethasone (BTM) into the urinary bladders of hydrochloric acid-induced micturition model rats.

Method

A chondroitin sulfate derivative prepared in compliance with the method of Example 2 was dissolved in phosphate-buffered saline to prepare the test substances indicated below.

Test Substances:
(1) Saline (control)
(2) 3% (w/v %) CS-βAla-BTM (BTM content: 34 w/w %)
(3) Mixture of 3% CS +0.86% BTM Rats (SD strain (SPF), females, age 10 to 13 weeks) were laparotomized under pentobarbital general anesthesia (40 mg/kg, i.p.) followed by incising the dome of the bladder and inserting a catheter (PESO) to construct a bladder fistula.

Cystitis was induced using 0.4 M hydrochloric acid. The rats were anesthetized and restrained in Bollman cages seven days after construction of the bladder fistula followed by connecting a urinary catheter, pressure transducer and syringe connected to a syringe pump in parallel. Normal intravesical pressure was measured while continuously infusing physiological saline (3 mL/h). 0.4 M hydrochloric acid was then continuously infused into the bladder for 15 minutes (3 mL/h) to induce micturition.

Two days after continuous instillation of hydrochloric acid, 0.2 mL of each test substance were administered transurethrally using a catheter (PESO) and retained in the bladder for 30 minutes under anesthesia.

Seven days after intravesical instillation of hydrochloric acid, the rats were restrained in Bollman cages followed by connecting a urinary catheter, pressure transducer and syringe connected to a syringe pump in parallel. Changes in intravesical pressure were measured while continuously infusing physiological saline (3 mL/h) starting 20 minutes after the animals emerged from anesthesia. Urinary function was evaluated by measuring intercontraction interval and single voided volume after changes in intravesical pressure had stabilized.

Figure 4:
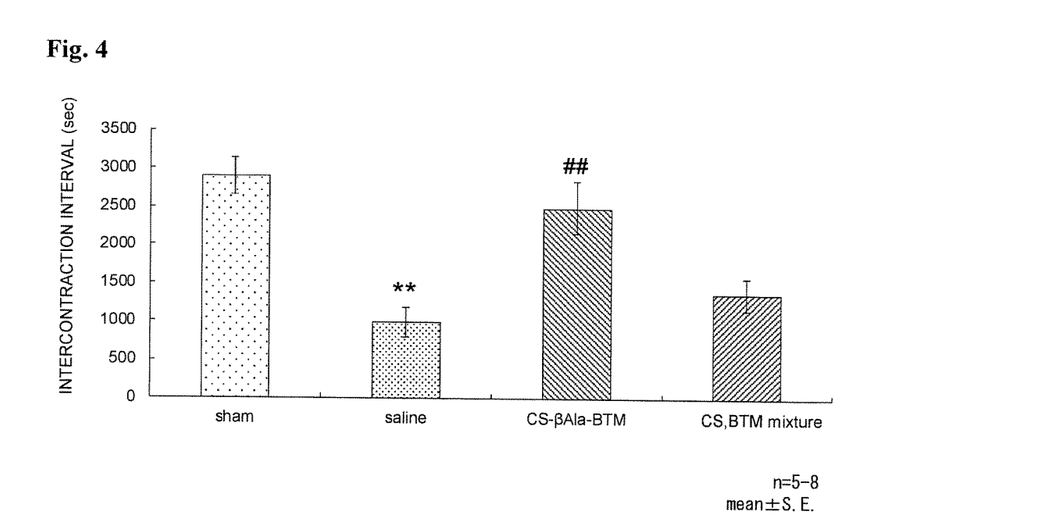
FIG. 4 is a graph indicating the effect of CS-β-alanyl-betamethasone and a mixture of CS and betamethasone on intercontraction interval in a rat hydrochloric acid-induced micturition model.

The results are shown in FIG. 4. In addition, changes in rat body weight are shown in Table 6. Furthermore, changes in body weight were measured under the same conditions as in Test Example B2.

TABLE 6

| Group | No. of Animals | Before Surgery (%) | Before induction with hydrochloric acid (%) | Before agent administration (%) | Before cystometry (%) |
|---|---|---|---|---|---|
| Sham | 6 | 100.0 ± 0.0 | 102.3 ± 0.6 | 99.6 ± 1.1 | 102.0 ± 1.5 |
| Saline | 5 | 100.0 ± 0.0 | 103.6 ± 1.2 | 100.0 ± 0.7 | 106.1 ± 1.2 |
| CS-βAla-BTM | 8 | 100.0 ± 0.0 | 102.5 ± 1.6 | 99.5 ± 1.3 | 101.7 ± 1.3 |
| CS + BTM Mixture | 5 | 100.0 ± 0.0 | 102.9 ± 1.0 | 98.3 ± 0.6 | 86.8 ± 0.3 |

Mean ± standard error (number of animals per group: 5 to 8)

Results

The results in FIG. 4 are indicated as average intercontraction interval±standard error (number of animals in each group: 5 to 8). In addition, double asterisks (**) indicate a level of significance of p<0.01 (vs. sham) according to the t-test. In addition, a double hash mark (##) indicates a level of significance of p<0.01 (vs. control) according to Dunnett's multiple comparison test.

According to FIG. 4, the CS-βAla-BTM administered group significantly increased intercontraction interval in comparison with the control group. On the other hand, the CS+BTM mixture administered group did not demonstrate effect that increases intercontraction interval. Similarly, with respect to single voided volume, although the CS-βAla-BTM administered group induced a significant increase in single voided volume in comparison with the control group, the CS+BTM mixture administered group did not demonstrate effect that significantly induces an increase in single voided volume.

According to Table 6, animals of the CS+BTM mixture administered group demonstrated prominent weight loss in comparison with the control group. On the other hand, the CS-βAla-BTM administered group was not observed to cause weight loss in comparison with the control group.

Discussion

CS-βAla-BTM clearly demonstrated effect that significantly improves urinary function following intravesical administration thereof in comparison with a CS+BTM mixture, and was determined to clearly reduce systemic adverse side effects attributable to steroids.

The entire content of the disclosure of Japanese Patent Application No. 2015-003572 (filing date: Jan. 9, 2015) is incorporated in the present specification by reference.

All references, patent applications and technical standards described in the present specification are incorporated in the present specification by reference to the same degree as in the case of the incorporation of individual references, patent applications and technical standards by reference being specifically and individually described.

INDUSTRIAL APPLICABILITY

The compound of the present invention is useful and can be applied industrially as a compound for improving bladder diseases.

The invention claimed is:

1. A method for treating bladder diseases comprising administration of a pharmaceutical composition to a subject having a bladder disease,
    wherein the pharmaceutical composition comprises a compound in which a group derived from chondroitin sulfate and a group derived from a steroid are covalently bonded together via a spacer represented by general formula (I):

—HN—(CH$_2$)$_m$—CHR$^1$—CO—      (I)

(in the formula, m represents an integer of 0 or 1, in the case m =0, R$^1$ represents a group selected from a group consisting of electron-donating groups and steric hindrance groups, and in the case m =1, R$^1$ represents a group selected from a group consisting of a hydrogen atom, electron-donating groups and steric hindrance groups).

2. The method according to claim 1, wherein, in general formula (I), the electron-donating groups and the steric hindrance groups represented by R$^1$ are groups selected from a group consisting of linear alkyl groups having 1 to 12 carbon atoms, branched alkyl groups having 3 to 12 carbon atoms, cyclic alkyl groups having 3 to 12 carbon atoms, aryl groups having 6 to 10 carbon atoms, alkenyl groups having 2 to 12 carbon atoms, alkynyl groups having 2 to 12 carbon atoms, and aralkyl groups having 7 to 12 carbon atoms.

3. The method according to claim 1, wherein, in general formula (I), m =1 and R$^1$ represents a hydrogen atom, or m =0 and R$^1$ represents a methyl group, branched alkyl group having 3 to 4 carbon atoms or benzyl group.

4. The method according to claim 1, wherein, in general formula (I), m =1 and R$^1$ represents a hydrogen atom, or m =0 and R$^1$ represents a sec-butyl group.

5. A method for improving urinary function comprising administration of a pharmaceutical composition to a subject having abnormal urinary function,
    wherein the pharmaceutical composition comprises a compound in which a group derived from chondroitin sulfate and a group derived from a steroid are covalently bonded together via a spacer represented by general formula (I):

—HN—(CH$_2$)$_m$—CHR$^1$—CO—      (I)

(in the formula, m represents an integer of 0 or 1, in the case m =0, R$^1$ represents a group selected from a group consisting of electron-donating groups and steric hindrance groups, and in the case m =1, R$^1$ represents a group selected from a group consisting of a hydrogen atom, electron-donating groups and steric hindrance groups).

6. The method according to claim 5, wherein, in general formula (I), the electron-donating groups and the steric hindrance groups represented by R$^1$ are groups selected from a group consisting of linear alkyl groups having 1 to 12 carbon atoms, branched alkyl groups having 3 to 12 carbon atoms, cyclic alkyl groups having 3 to 12 carbon atoms, aryl groups having 6 to 10 carbon atoms, alkenyl groups having 2 to 12 carbon atoms, alkynyl groups having 2 to 12 carbon atoms, and aralkyl groups having 7 to 12 carbon atoms.

7. The method according to claim 5, wherein, in general formula (I), m =1 and R$^1$ represents a hydrogen atom, or m =0 and R$^1$ represents a methyl group, branched alkyl group having 3 to 4 carbon atoms or benzyl group.

8. The method according to claim 5, wherein, in general formula (I), m =1 and R$^1$ represents a hydrogen atom, or m =0 and R$^1$ represents a sec-butyl group.

* * * * *

UNITED STATES PATENT AND TRADEMARK OFFICE
CERTIFICATE OF CORRECTION

Page 1 of 2

PATENT NO. : 10,350,236 B2
APPLICATION NO. : 15/542226
DATED : July 16, 2019
INVENTOR(S) : Muneto Narita et al.

It is certified that error appears in the above-identified patent and that said Letters Patent is hereby corrected as shown below:

In the Specification

Column 2, Line 49, "R'" should read -- $R^1$ --, and

Column 2, Line 66, "R'" should read -- $R^1$ --, and

Column 4, Line 6, "CSβ-" should read -- CS-β- --, and

Column 4, Line 41, "R'" should read -- $R^1$ --, and

Column 4, Line 43, "R'" should read -- $R^1$ --, and

Column 5, Line 45, "folioed" should read -- formed --, and

Column 5, Line 57, "(13 HN—" should read -- (—HN— --, and

Column 8, Line 53, "spacer-fanning" should read -- spacer-forming --, and

Column 15, Line 28, "21 -(Boc" should read -- 21-(Boc --, and

Column 19, Line 37, "CSβ" should read -- CS-β --, and

Column 19, Line 52, "5.0" should read -- 5.0% --, and

In the Claims

Column 26, Claim 2, Line 1, "10carbon" should read -- 10 carbon --, and

Column 26, Claim 2, Line 2, "12carbon" should read -- 12 carbon --, and

Signed and Sealed this
First Day of October, 2019

Andrei Iancu
*Director of the United States Patent and Trademark Office*

CERTIFICATE OF CORRECTION (continued)
U.S. Pat. No. 10,350,236 B2

Column 26, Claim 4, Line 9, "R¹represents" should read -- $R^1$ represents --, and Column 26, Claim 5, Line 22, "R¹represents" should read -- $R^1$ represents --, and Column 26, Claim 6, Line 34, "10carbon" should read -- 10 carbon --, and Column 26, Claim 6, Line 35, "12carbon" should read -- 12 carbon --, and Column 26, Claim 7, Line 38, "R¹represents" should read -- $R^1$ represents --.